(12) United States Patent
Grayson

(10) Patent No.: US 8,318,809 B2
(45) Date of Patent: Nov. 27, 2012

(54) COMPOSITIONS AND METHODS FOR TREATING JELLYFISH STINGS

(76) Inventor: John C. Grayson, Savannah, GA (US)

(*) Notice: Subject to any disclaimer, the term of this patent is extended or adjusted under 35 U.S.C. 154(b) by 605 days.

(21) Appl. No.: 12/442,144

(22) PCT Filed: Sep. 21, 2007

(86) PCT No.: PCT/US2007/079180
§ 371 (c)(1),
(2), (4) Date: Mar. 20, 2009

(87) PCT Pub. No.: WO2008/036912
PCT Pub. Date: Mar. 27, 2008

(65) Prior Publication Data
US 2010/0010085 A1 Jan. 14, 2010

Related U.S. Application Data

(60) Provisional application No. 60/846,195, filed on Sep. 21, 2006.

(51) Int. Cl.
*A01N 33/00* (2006.01)
*A01N 37/18* (2006.01)
*A01N 33/02* (2006.01)
*A61K 31/13* (2006.01)
*A61K 31/16* (2006.01)
*A61K 31/135* (2006.01)
(52) U.S. Cl. ............ 514/579; 514/613; 514/646
(58) Field of Classification Search ............ 514/534, 514/579, 613, 646
See application file for complete search history.

(56) References Cited

U.S. PATENT DOCUMENTS 4,478,853 A * 10/1984 Chaussee ............ 514/772
6,048,855 A * 4/2000 De Lacharriere et al. ............ 514/213.01

* cited by examiner

*Primary Examiner* — Yong Chong
(74) *Attorney, Agent, or Firm* — McClure, Qualey & Rodack, LLP

(57) ABSTRACT

Methods and compositions for treating skin conditions, in particular jellyfish stings, are provided.

4 Claims, 2 Drawing Sheets

COMPOSITIONS AND METHODS FOR TREATING JELLYFISH STINGS

CROSS REFERENCE TO RELATED APPLICATION

This application claims the benefit of U.S. Provisional Application No. 60/846,195, filed Sep. 21, 2006, which is hereby incorporated by reference.

BACKGROUND

Jellyfish stings are hazardous for anyone who enters a marine environment anywhere in the world. Jellyfish are most common in the tropics, but are found in waters ranging from tropical to arctic. Stings are more common in the summer months due to the increased recreational exposure to the marine environment as well as the seasonal patterns of jellyfish.

Recent increases in the jellyfish population have made jellyfish stings a more frequent occurrence, and a more common concern for would-be swimmers. Some marine scientists attribute the recent proliferation of jellyfish to mankind's impact on marine life; jellyfish may merely be taking the place of already overfished creatures. Since jellyfish feed on the same kinds of prey as many species of fishes, depletion of fish populations allows jellyfish to move in. Sampling sea life in certain heavily fished regions has shown that jellyfish have actually overtaken fish in terms of the biomass they contribute to these ocean regions. Additionally, increased nutrients in the water, ascribed to agricultural runoff and urban by-products, may also be a factor in the recent proliferation of jellyfish numbers. High levels of nutrients provide nourishment for the small organisms on which jellyfish feed. In waters where there is eutrophication, low oxygen levels often result, favoring jellyfish, which thrive in less oxygen-rich water than fish can tolerate.

Jellyfish, or coelenterates, are marine invertebrates belonging to the Scyphozoan class, and in turn the phylum Cnidaria. They are related to corals, hydra and sea anemones. The body of an adult jellyfish is composed of a bell-shaped, jellylike substance enclosing its internal structure, from which the creature's tentacles suspend. Each tentacle is covered with stinging cells (cnidocytes) that can sting or kill other animals: most jellyfish use them to secure prey or as a defense mechanism. In its adult form, a jellyfish is composed of 94-98% water and can be found in every pelagic area of the world.

Most jellyfish have tentacles or oral arms coated with thousands of the stinging cells called cnidocytes containing a microscopic, toxin-filled harpoon, a nematocysts. Generally, each nematocyst has a "trigger" (cnidocil) paired with a capsule containing a coiled stinging filament, as well as barbs on the exterior. Upon contact, the filament will swiftly unwind, launch into the target, and inject toxins. It can then pull the victim into its mouth, if appropriate. In addition to discharging toxin, the nematocysts activate the surrounding cnidocytes to increase the total volume of venom injected. Importantly, the nematocysts are still able to function when separated from the jellyfish, making deactivation and removal of these stingers a key element of treatment.

There are several types of coelenterate toxins, but all consist of a complex mixture of proteins and enzymes. The most severe envenomations can occasionally induce systemic responses such as nausea, headache, and chills and even more rarely can induce severe systemic reactions such as cardiac arrhythmia, respiratory dysfunction, psychosis, and muscular spasm. Yet the major feature of most stings is the rash and associated pain, which is caused by a combination of several elements of the venom. Most envenomations result in pain that can be severe, but is usually self-limited. The duration of the symptoms of minor stings ranges from a few minutes to several hours, weeks, or longer depending upon the jellyfish species, the extent of the sting, the presenting symptoms, and the physiology of the individual. Most of the effects, both mild and severe, are caused by the actions of the venom, not an allergic reaction. The local reaction to most jellyfish envenomations includes local reactions such as pain, pruritus, paresthesias such as numbness, burning, or throbbing, inflammatory rash, blistering, and swelling.

Common anecdotal treatment of an envenomation is the liberal application of 5 percent acetic acid (household vinegar) to the affected areas. The acetic acid is supposed to deactivate any non-discharged nematocysts, however the results below indicate that application of vinegar may actually trigger firing of additional nematocysts. Additionally, the nematocysts of certain species of jellyfish may not be effectively deactivated by vinegar. Other topical decontaminants such as baking soda, isopropyl alcohol, a paste of meat tenderizer or papaya, concentrated citrus juice, olive oil and quarter strength household ammonia are often recommended, but have varying or little effectiveness. Fresh water or an organic solvent such as gasoline or turpentine must not be applied. Such agents may cause the firing of more nematocysts and worsen the sting or damage the skin directly.

After deactivation, general treatment protocols recommend that the sting area should be exposed and any remaining tentacles or nematocysts removed. Various techniques for removal are recommended, from rubbing with sand or a paste of mud or sand (which has been shown to induce additional nematocyst firing and increase pain), to shaving the affected area with shaving cream and a razor or other available object such as a credit card or seashell. However, most of these traditional or "home" remedies prove slow-acting and/or ineffective at best, and at worst, some of the above remedies can result in the release of more toxin and an increase in pain. Meanwhile, the patient continues to experience pain and other symptoms of the sting for several hours or days.

No commercial preparations for the treatment of jellyfish stings appear to exist, and topical preparations for other skin conditions such as sunburn prove ineffective. While the above-described traditional remedies, such as vinegar, may have limited deactivating properties, such formulations still lack an effective pain relief, particularly in the short term. Thus, presently a formulation that adequately and quickly treats the pain and swelling associated with jellyfish stings, and other animal stings and skin irritations is not available and would be desirable for at least the above reasons.

SUMMARY

The present disclosure provides compositions and methods that overcome at least the above deficiencies. The methods of the present disclosure include treating jellyfish stings or other skin conditions with a pharmaceutical formulation for the treatment of jellyfish stings (e.g., stings of species of Scyphozoa jellyfish, such as, but not limited to, *Chiropsalmus quadumanus* or "sea wasp", and *Chrysaora quinquecirrha*, commonly called the sea nettle, and the like), as well as other stings (e.g., insect, ant, wasp, etc.) and skin irritations (poison ivy, contact dermatitis, etc.). The compositions of the present disclosure are formulations that include an active agent including a topically active local anesthetic compound (e.g., lidocaine, benzocaine, and the like), and an effective carrier. The compositions may optionally also include, but is not limited to, antiseptic compounds, compounds to increase solubility of the active agent, and/or other inactive ingredients, such as, but not limited to, preservatives and fragrant compounds for providing a pleasant aroma. Embodiments of the present disclosure also include formulations consisting essentially of and compounds consisting of a topically active local anesthetic compound, an effective carrier and, optionally, solubilizers, antiseptic compounds, and aromatic compounds.

The formulations may be in various topical dosage forms such as solutions, suspensions, gels, ointments, creams, powders, and the like. In exemplary embodiments the formulation is a solution or suspension to be administered as drops or spray to the affected area. In other embodiments the formulation is an ointment, cream, or gel for application to the affected area. The carrier component may be selected and/or compounded to provide the composition in the form desired.

The present disclosure also provides methods of treating jellyfish stings and other painful and/or uncomfortable skin conditions with the compositions of the present disclosure. In particular embodiments, the methods provide for treating jellyfish stings, particularly for providing immediate pain relief from one or more jellyfish stings. While particularly useful for relieving pain and discomfort associated with jellyfish stings, the formulations of the present disclosure are also useful for treating any other painful or irritating skin condition, such as stings of other organisms (ants, wasps, mosquitoes, and other insects and stinging organisms), skin rashes and reactions to plant toxins (poison ivy, poison oak, and the like), contact dermatitis from allergic reactions and other skin conditions such as sunburn. In particular, the formulations of the present disclosure are useful for treating insect bites that are difficult to treat conventionally, such as chiggers (*Trombicula alfreddugesi*) ("red bugs") and fire ants.

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

BRIEF DESCRIPTION OF THE DRAWINGS

The disclosure can be better understood with reference to the following drawings.

DETAILED DESCRIPTION

Figure 1:
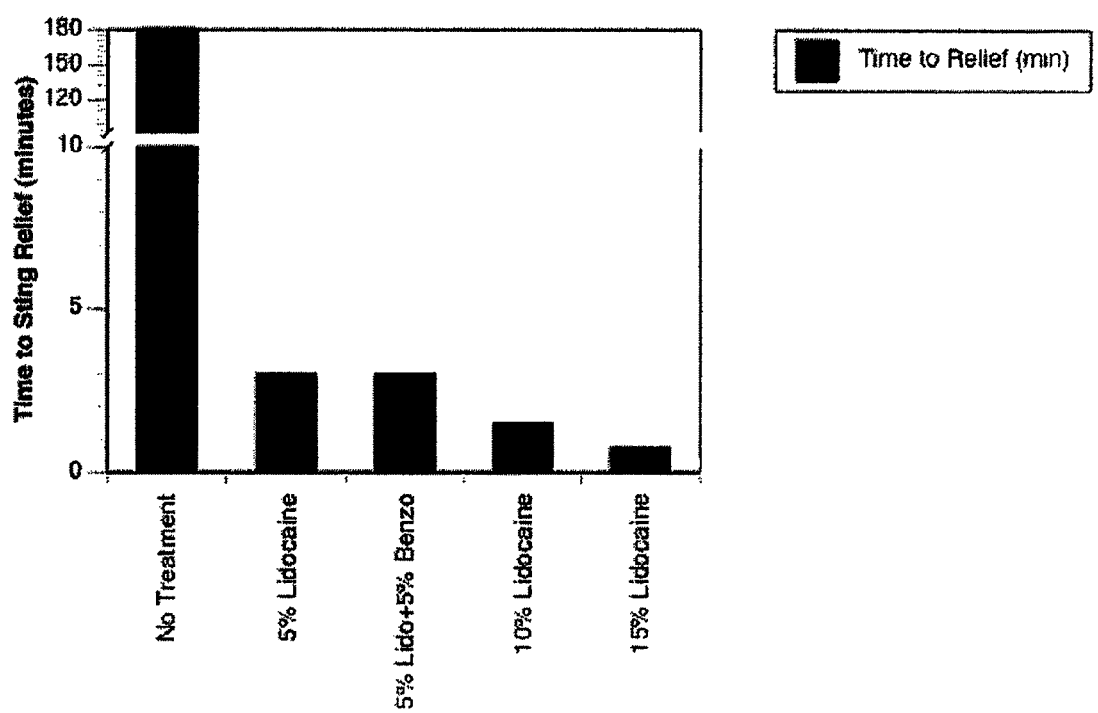
FIG. 1 illustrates a bar graph showing the time to sting relief exhibited by formulations according to the present disclosure having various concentrations of lidocaine or a lidocaine/benzocaine mixture.

Embodiments of the present disclosure will employ, unless otherwise indicated, techniques of medicine, organic chemistry, biochemistry, molecular biology, marine biology, pharmacology, and the like, that is within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless stated to the contrary, the percentages stated hereinafter are weight percentages, e.g., grams of material per 100 milliliters of solution, or, for hydrogels, grams of material per 100 grams of final product. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular components, reagents, additives, reaction materials, compounding processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an" and "the" include plural referents unless the context clearly dictates otherwise. Thus, for example, reference to "a support" includes a plurality of supports.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

All patents, patent applications, and publications mentioned herein are hereby incorporated by reference in their entireties.

Definitions:

In this specification and in the claims that follow, reference will be made to a number of terms that shall be defined to have the following meanings unless a contrary intention is apparent.

The term "organism" or "host" refers to any living entity comprised of at least one cell. A living organism can be as simple as, for example, a single eukaryotic cell or as complex as a mammal, including a human being. As used herein, the term "host" includes humans, mammals (e.g., cats, dogs, horses, chicken, pigs, hogs, cows, and other cattle), and other living species that are in need of treatment. In particular, the term "host" includes humans.

The term "derivative" refers to a modification to the disclosed compounds.

The term "therapeutically effective amount" as used herein refers to that amount of the compound being administered which will relieve to some extent one or more of the symptoms of the disorder being treated. In reference to a jellyfish sting, a therapeutically effective amount refers to that amount which has the effect of (1) reducing the amount of pain associated with the sting, (2) inhibiting (that is, slowing to some extent, preferably stopping) any further firing by the nematocysts, and/or, (3) relieving to some extent (or, preferably, eliminating) one or more additional symptoms associated with the sting, such as, but not limited to redness, swelling, formation of whelps, blisters, and/or hives, and itching. In reference to other dermatological conditions that may be treated with the compositions of the present disclosure, a therapeutically effective amount refers to that amount which has the effect of (1) reducing the amount of pain associated with the condition and/or relieving to some extent (or, preferably, eliminating) one or more additional symptoms associated with the condition, such as, but not limited to redness, swelling, formation of whelps and/or hives, and itching "Pharmaceutically acceptable salt" refers to those salts which retain the biological effectiveness and properties of the free bases and which are obtained by reaction with inorganic or organic acids such as, but not limited to, hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or a pharmaceutically acceptable salt thereof, with other chemical components, such as physiologically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound. "Carriers" as used herein include pharmaceutically acceptable carriers, excipients, or stabilizers which are nontoxic to the host being exposed thereto at the dosages and concentrations employed.

An "excipient" refers to an inert substance added to a pharmaceutical composition to further facilitate administration of a compound. Examples, without limitation, of excipients include calcium carbonate, calcium phosphate, various sugars and types of starches, cellulose derivatives, gelatin, vegetable oils, and polyethylene glycols.

"Treating" or "treatment" of a condition includes inhibiting the condition (slowing or arresting its development), providing relief from the symptoms or side-effects of the condition (including palliative treatment), and relieving the condition (causing regression of the condition). With regard to stings and/or bites, particularly jellyfish stings, these terms mean that the pain associated with the sting is reduced and/or eliminated, and/or that one or more of other symptoms associated with the sting (e.g., redness, swelling, and itching) will be reduced. With regard to other dermatological conditions, these terms mean that that the pain associated with the condition is reduced and/or eliminated, and/or that one or more of other symptoms associated with the condition (e.g., redness, swelling, and itching) will be reduced.

As used herein, the term "topically active agents" refers to compositions of the present disclosure that elicit pharmacological responses at the site of application (contact) to a host.

As used herein, the term "topically" refers to application of the compositions of the present disclosure to the surface of the skin and mucosal cells and tissues.

The disclosed compounds can form salts that are also within the scope of this disclosure. Reference to each compound herein is understood to include reference to salts thereof, unless otherwise indicated. The term "salt(s)," as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful (e.g., in isolation or purification steps which may be employed during preparation). Salts of the compounds may be formed, for example, by reacting the compound with an amount of acid or base, such as an equivalent amount, in a medium such as one in which the salt precipitates or in an aqueous medium followed by lyophilization.

The disclosed compounds that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates (such as tosylates), undecanoates, and the like. Particularly, hydrochloride salts of the disclosed compounds may be used in embodiments of the present disclosure.

The disclosed compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dihydroabietyl)ethylenediamine), N-methyl-D-glucamines, N-methyl-D-glucamides, t-butyl amines, and salts with amino acids such as arginine, lysine, and the like.

Solvates of the compounds are also contemplated herein. Solvates of the compounds are preferably hydrates.

To the extent that the disclosed compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The term "formulation" or "pharmaceutical formulation" generally refers to any mixture, solution, suspension, gel, ointment, or the like which contains the active compounds of the present disclosure and a carrier, and any additional optional inactive ingredients and is in a form suitable for delivery to a host in need of treatment. Thus, the term "formulation" includes various dosage forms of compositions of the present disclosure.

As used herein, the term "consisting essentially of" indicates that the referenced composition includes the listed ingredients and no other active ingredients or other ingredients that may affect the activity of the primary ingredients. For instance, the composition may include certain impurities or inert ingredients that do not effect the activity of the composition. In addition, any such inert ingredients should not increase the sensation of pain, itching, or other symptom of the condition being treated.

Discussion:

Methods of the present disclosure include treatment of dermatological conditions, in particular jellyfish stings, with compositions of the present disclosure. The compositions of the present disclosure include pharmaceutical formulations that include a topically active local anesthetic compound and an effective carrier. The compositions may optionally also include other appropriate pharmaceutically acceptable components such as excipients, solubilizers, stablilizers, surfactants, tonicity agents, viscosity modifying agents, buffers, fragrances, preservatives, and the like. The formulations may be in various topical dosage forms such as solutions, suspensions, gels, ointments, creams, powders, and the like.

The amount of topically active local anesthetic of the present disclosure depends on the purpose of the use, e.g., the treatment of jellyfish stings or other conditions. The amount utilized also depends on the particular tissues being treated. For example, lower concentrations typically are utilized to treat especially sensitive tissue while somewhat higher concentrations may be utilized to treat less sensitive tissues. The concentrations determined to be necessary for the above-stated purposes can be functionally described as "a therapeutically effective amount" or a "pharmaceutically effective amount", or variations thereof.

The analgesic compounds in the compositions of the present disclosure include topically effective local anesthetics. In some embodiments the local anesthetics component is chosen based upon topical activity in combination with a lack of toxicity. In particular embodiments, the topically effective local anesthetic is selected from the class of local anesthetics including aminoamide and aminoester local anesthetics. An exemplary aminoamide compound that may be utilized according to the present disclosure includes, but is not limited to, lidocaine. An exemplary aminoester compound that may be utilized according to the present disclosure includes, but is not limited to, benzocaine. In preferred embodiments, the composition includes lidocaine, benzocaine, or both.

In an exemplary embodiment of a solution or suspension of the composition of the present disclosure (to be used in drop or spray form), the local anesthetic compound is benzocaine. The benzocaine compound may include the benzocaine itself or pharmaceutically acceptable salts thereof, including acid addition salts such as hydrochlorides and the like. The amounts of topically active benzocaine utilized generally is in the range of from about 1% to 25%, more preferably from about 5% to 15%.

In an another exemplary embodiment of a solution or suspension of the composition of the present disclosure (to be used in drop or spray form), the local anesthetic compound is lidocaine. The lidocaine compound may include the lidocaine itself or pharmaceutically acceptable salts thereof, including acid addition salts such as hydrochlorides (e.g., lidocaine hydrochloride) and the like. The amounts of topically active lidocaine utilized generally is at least about 2.75%, preferably at least about 4%. In some embodiments the amount of lidocaine is in the range of from about 4% to 25%, about 4% to 30%, or from about 10% to 15%.

Where such forms exist, the local anesthetic compounds may include pharmaceutically acceptable analogues, homologues, isomers, or derivatives thereof. In addition, the compounds of the present disclosure can include pharmaceutically acceptable salts, esters and derivatives of the local anesthetic compounds described above. Pharmaceutical compositions and dosage forms of the disclosure may include a pharmaceutically acceptable salt of the compound and/or a pharmaceutically acceptable polymorph, solvate, hydrate, dehydrate, co-crystal, anhydrous, or amorphous form thereof.

Pharmaceutical unit dosage forms of the compounds of this disclosure are suitable for topical administration to a patient. Examples of dosage forms include, but are not limited to: liquid dosage forms suitable for topical administration to a patient, including suspensions (e.g., aqueous or non-aqueous liquid suspensions, oil-in-water emulsions, or water-in-oil liquid emulsions), solutions, pastes, powders, creams, or aerosols.

Exemplary embodiments include pharmaceutical compositions that can be manufactured by processes well known in the art (e.g., by means of conventional mixing, dissolving, granulating, dragee-making, levigating, emulsifying, encapsulating, entrapping, lyophilizing processes or spray drying). Such formulations include solutions, suspensions, drops, sprays, ointments, creams, gels, and the like. The formulations may be aqueous or nonaqueous, but will generally be aqueous.

The composition, shape, and type of dosage forms of the compositions of the disclosure typically vary depending on their use. For example, a dosage form used in the acute treatment of a condition or disorder in adults may contain larger amounts of the active ingredient, e.g., the disclosed compounds or combinations thereof, than a dosage form used in the treatment of the same condition or disorder for children. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

The compositions of the present disclosure can be liquids or lyophilized or otherwise dried formulations and may include diluents of various buffer content (e.g., Tris-HCl, acetate, and phosphate), pH and ionic strength, additives such as albumin or gelatin to prevent absorption to surfaces, a surfactant such as a polysorbate surfactant (e.g., TWEEN 20, TWEEN 40, TWEEN 60, and TWEEN 80), a phenoxypolyethoxyethanol surfactant (e.g., TRITON X-100, X-301, X-165, X-102, and X-200, and TYLOXAPOL) Pluronic F68, or sodium dodecyl sulfate, solubilizing agents (e.g., glycerol, polyethylene glycerol), anti-oxidants (e.g., ascorbic acid, sodium metabisulfite), preservatives (e.g., Thimerosal, benzyl alcohol, benxalkonium chloride, DMDM Hydantoin, and parabens such as methyl paraben and propyl paraben), bulking substances, tonicity modifiers (e.g., lactose, and mannitol) as well as other inactive ingredients such as fragrances (e.g., eucalyptus oil, camphor, and the like) and other counterirritants, such as aloe extracts (e.g., aloe barbandensis leaf juice). Some formulations may also include materials to aid in incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions can influence the physical state, solubility, stability, rate of in vivo release, and rate of in vivo clearance, controlled or sustained release compositions include formulation in lipophilic depots (e.g., fatty acids, waxes, and oils).

Since it is known that certain local anesthetic agents that may be included in the compositions of the present disclosure, such as lidocaine and benzocaine, are sparingly soluble in water, the solubility of such compounds may be increased by use of solubilizers such as acetone, ethanol, and propylene glycol. In exemplary embodiments of the present disclosure lidocaine is solubilized by combination with one or more of acetone, ethanol, propylene glycol and water, and benzocaine is solubilized by combination with acetone, ethanol, propylene glycol. In other exemplary embodiments, pharmaceutically acceptable salts of the local anesthetic agents may be used to improve the solubility in water. For instance, in some exemplary embodiments, lidocaine hydrochloride (e.g., lidocaine hydrochloride monohydrate) may be used, as it is soluble in water.

Other embodiments provide particulate compositions coated with polymers (e.g., poloxamers or poloxamines). Still other embodiments of the compositions incorporate particulate forms, protective coatings, protease inhibitors or permeation enhancers for various routes of administration, including epidermal. In certain embodiments the pharmaceutical composition is administered topically via the skin as drops, spray, ointment, gel or in any other form effective to deliver active compositions.

For topical applications, the pharmaceutically acceptable carrier may take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Further, as used herein "pharmaceutically acceptable carriers" are well known to those skilled in the art and include, but are not limited to, water, about 0.01-0.1M and 0.05M phosphate buffer or about 0.8% saline. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Preservatives and other additives may also be present, such as, for example, antimicrobials, antioxidants, collating agents, inert gases and the like.

Controlled or sustained release compositions may include a formulation of the disclosure in lipophilic depots (e.g., fatty acids, waxes, and oils). Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit longer half-lives than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Examples of suitable oily vehicles or solvents for use with the present disclosure are vegetable or animal oils such as sunflower oil or fish-liver oil. For formulation in liquid form for application in drop or spray form the compositions or their physiologically tolerated derivatives such as salts, esters, N-oxides, and the like are converted into a solution, suspension, or emulsion, if desired, with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers.

In addition, if desired, the composition can contain minor amounts of auxiliary substances such as wetting or emulsifying agents, or pH buffering agents that enhance the effectiveness of the active ingredient. Generally the pH of formulations of the present disclosure vary from about 4.0 to 8.0; preferably the pH of the formulation is about 6.0.

An active component can be formulated into the composition as neutralized pharmaceutically acceptable salt forms. Pharmaceutically acceptable salts include the acid addition salts (formed with the free amino groups of the polypeptide or antibody molecule), which are formed with a pharmaceutically acceptable acid such as, for example, hydrochloric acid, sulphuric acid, methanesulphonic acids, fumaric acid, maleic acid, succinic acid, acetic acid, benzoic acid, oxalic acid, citric acid, tartaric acid, carbonic acid, phosphoric acid and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, sprays, drops, and the like, the active compounds or their physiologically tolerated derivatives such as salts, esters, N-oxides, and the like are prepared and applied as solutions, suspensions, or emulsions in a physiologically acceptable diluent with or without a pharmaceutical carrier.

The compositions also include a carrier, for example a pharmaceutically acceptable carrier, as discussed above. Often the physiologically acceptable carrier is an aqueous pH buffered solution. Examples of physiologically acceptable carriers include water; buffers such as phosphate, borate, citrate and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), propylene glycol, and PLURONICS™. The carrier can also include water or a mild or dilute saline solution, preferably a physiologically balanced saline solution. Additionally, the ion concentration of the carrier can be adjusted to provide a mild antibacterial effect. Saline solutions are also commonly used as moisturizers. In an exemplary embodiment of the composition of the present disclosure, the carrier is water. In other exemplary embodiments of the present disclosure, the carrier is a mixture of water and propylene glycol. The amounts of carrier utilized generally are in the range of from about 20% to 98%, more preferably from about 50% to 85%, most preferably from about 60% to 80%.

In addition, compositions of the present disclosure may also include one or more antiseptic and/or preservative agents, such as, but not limited to, phenol. Other possible antiseptic and/or preserving agents include, but are not limited to, benzalkonium chloride and benzethonium chloride, DMDM Hydantoin, and parabens such as, but not limited to, methyl paraben and propyl paraben. In some exemplary embodiments, the formulation may include from about 0.01% to 2% of a preservative and/or antiseptic agent, preferably from about 0.05% to 1% or a preservative and/or antiseptic agent. Various inactive components may also be added. For instance one or more aromatic compounds may also be added for fragrance. Exemplary fragrant compounds include camphor and the like (menthol, eucalyptus, peppermint, tee tree oil, etc.). Sometimes such fragrant compounds may provide additional benefits such as counterirritant properties (e.g., cooling sensation, etc.). Particularly in embodiments including phenol, which has a distinct odor, it may be preferable to include one or more fragrant compounds. In some exemplary embodiments, the formulation includes from about 0.01% to 1% of a fragrant compound (e.g., camphor, eucalyptus oil, menthol, peppermint oil, tee tree oil, combinations thereof, and the like). Other compounds may also be added for additional counterirritant or soothing properties, such as aloe extracts (e.g., aloe barbadensis leaf juice). In some embodiments, aloe is included in an amount of about 0.01% to 1% of the composition.

Some exemplary formulations according to the present disclosure for use in treating jellyfish stings and other stings and/or skin irritations are presented below in Table 1. Lidocaine (as lidocaine or lidocaine hydrochloride) and/or benzocaine are used as topically active anesthetic agents; water and/or a mixture of water and propylene glycol is used as a solvent/carrier; phenol, benzalkonium chloride, DMDM Hydantoin, methyl paraben, propyl paraben or a combination thereof, is used as an antiseptic agent; camphor and/or eucalyptus oil is used as an aromatic agent for fragrance; and, optionally, aloe barbadensis leaf juice is included for additional soothing properties. In some of the formulations presented in Table 1 below, the lidocaine and/or benzocaine is first dissolved in acetone (up to about 12.5%, although a greater percentage could be used) then diluted with propylene glycol as the carrier. As used in Table 1 below "lidocaine" may be either lidocaine or lidocaine hydrochloride; when water is the only solvent used, the lidocaine is lidocaine hydrochloride.

TABLE 1

| Formula | Ingredients | Amount (w/v %) |
|---|---|---|
| general | lidocaine | 5-20 |
| | benzocaine | 0-5 |
| | acetone | 0-12.5 |
| | phenol | 0-0.1 |
| | benzalkonium chloride | 0-0.1 |
| | DMDM hydantoin | 0-0.5 |
| | methyl paraben | 0-0.5 |
| | propyl paraben | 0-0.1 |
| | aloe barbadensis leaf juice | 1-0.1 |
| | camphor | 0-0.1 |
| | eucalyptus oil | 0-0.1 |
| | propylene glycol | 0-50% |
| | water | carrier |
| 1 | lidocaine | 20 |
| | phenol | .05-1 |
| | camphor | 0-0.1 |
| | water | carrier |
| 2 | lidocaine | 15 |
| | phenol | .05-1 |

TABLE 1-continued

| Formula | Ingredients | Amount (w/v %) |
|---|---|---|
| | camphor | 0-0.1 |
| | water | carrier |
| 3 | lidocaine | 15 |
| | benzocaine | 1 |
| | phenol | .05-1 |
| | camphor | 0-0.1 |
| | water | carrier |
| 4 | lidocaine | 10 |
| | phenol | .05 |
| | camphor | 0-0.1 |
| | water | carrier |
| 5 | lidocaine | 10 |
| | benzocaine | 1 |
| | phenol | .05-1 |
| | camphor | 0-0.1 |
| | water | carrier |
| 6 | lidocaine | 5 |
| | phenol | .05-1 |
| | camphor | 0-0.1 |
| | water | carrier |
| 7 | lidocaine | 5 |
| | benzocaine | 1 |
| | phenol | .05-1 |
| | camphor | 0-0.1 |
| | water | carrier |
| 8 | lidocaine | 10-15 |
| | phenol | .05-1 |
| | camphor | 0-0.1 |
| | propylene glycol | 15 |
| | water | carrier |
| 9 | lidocaine (dissolved in acetone) | 5 |
| | benzocaine (dissolved in acetone) | 5 |
| | phenol | .05-1 |
| | camphor | 0-0.1 |
| | propylene glycol | carrier |
| 10 | lidocaine | 10 |
| | phenol | .05-1 |
| | camphor | 0-0.1 |
| | 50:50 water:propylene glycol | carrier |
| 11 | lidocaine | 10-15 |
| | water | carrier |
| 12 | lidocaine | 10-15 |
| | propylene glycol | 15 |
| | water | carrier |
| 13 | lidocaine | 10-15 |
| | 50:50 water:propylene glycol | carrier |
| 14 | lidocaine (dissolved in acetone) | 5 |
| | benzocaine (dissolved in acetone) | 5 |
| | propylene glycol | carrier |
| 15 | lidocaine | 4 |
| | water | carrier |
| 16 | lidocaine | 4 |
| | eucalyptus oil | 0.01 |
| | aloe barbadensis leaf juice | 0.01 |
| | benzalkonium chloride | 0.05 |
| | water | carrier |
| 17 | lidocaine | 4 |
| | eucalyptus oil | 0.01 |
| | aloe barbadensis leaf juice | 0.01 |
| | DMDH hydantoin | 0.4 |
| | methyl paraben | 0.2 |
| | propyl paraben | 0.05 |
| | water | carrier |

The present disclosure also provides methods of treating epidermal conditions by administering a therapeutically effective amount of the above compositions to a patient in need of treatment. In particular, the present disclosure provides methods for treating jellyfish stings, stings of other organisms (e.g., insects such as chiggers, fire ants, and the like), and other painful dermatological conditions in a host. The sting, bite or other condition may occur on any area of the patient's skin. Some of the formulations described in the examples below were intended for the treatment of jellyfish stings, but would be appropriate, with minimal to no modifications, for treating other stings, bites, sunburns, contact dermatitis, and other painful skin conditions as well. The ointment preparations described below are also intended for the treatment of such stings and other skin conditions.

The amounts and specific type of active ingredient in a dosage form may differ depending on various factors. The specific therapeutically effective dose level for any particular host depends upon a variety of factors, including for example, the disorder being treated and the severity of the disorder; activity of the specific composition employed; the specific composition employed, the age, body weight, general health, sex, and diet of the host; the time of administration; route of administration; rate of excretion of the specific compound employed; the duration of the treatment; drugs used in combination or coincidental with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions of the present disclosure are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium. Preferred unit dosage formulations are those containing a daily dose or unit, daily sub-dose, or an appropriate fraction thereof, of the administered ingredient. Appropriate dosages depend upon the specific dosage form used, but by way of example, approximately 4 to 10 drops (or the rough equivalent in a spray form, or the amount required to cover the affected area) of a pharmaceutical composition (in a drop dosage form) of the present disclosure applied as soon as possible, preferably immediately, after the sting occurs can effectively treat the pain and/or swelling associated with a common jellyfish sting in a human. Similarly, a generally thin coverage application of an ointment dosage form of the pharmaceutical composition of the present disclosure applied after the sting can also effectively treat the pain and/or swelling associated with the sting in a human.

As described in the examples below, various embodiments of formulations of the present disclosure have been tested on jelly fish stings on numerous subjects with average results providing substantial to complete relief from pain within 30 seconds to 5 minutes from the application, depending on factors such as the type and percentage of anesthetic agent used. Other symptoms such as swelling, redness, and itching were also reduced and/or eliminated by application of the formulations of the present disclosure to the affected area. In other examples described below, an embodiment of a formulation according to the present disclosure was also tested for effectiveness on other conditions, in particular, bites inflicted by fire ants and chiggers. The formulation was found to provide substantial to complete relief from the associated symptoms (pain, itching, blistering) by the subjects tested.

It should be emphasized that the above-described embodiments of the present disclosure are merely possible examples of implementations and are merely set forth for a clear understanding of the principles of the disclosure. Many variations and modifications may be made to the above-described embodiment(s) of the disclosure without departing substantially from the principles of the disclosure. All such modifications and variations are intended to be included herein within the scope of the present disclosure and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

EXAMPLES

Example 1

Jellyfish Sting Testing Materials

Test Organisms

Two genera of jellyfish were used in examples 2-19 described below: *Chiropsalmus quadumanus*, a cubomedusa and member of the Scyphozoa, also known as the sea wasp; and another scyphozoan jellyfish, *hrysaora quinquecirrha*, commonly called the sea nettle. These are the two most common types of stinging jellies that occur with frequency and/or regularity in normal swimming waters on the USA east coast north of Cape Canaveral.

Living healthy specimens were captured locally using trawls and dip-nets. They were maintained in flowing seawater aquariums (ca. 500 liters) for days-weeks; sea nettles maintained for long periods were fed live minnows (mummichugs).

Compounds

The following compounds were used in formulations tested in examples 2-19. The compounds and their sources are listed in Table 2, below, along with the various concentrations of the compounds used in the formulations tested.

TABLE 2

| Chemical tested/use | Supplier & Number | Concentrations |
| --- | --- | --- |
| Lidocaine | Sigma (L7757-25g) | 5% in ethanol/propylene glycol (5:95 w/w) |
| Lidocaine hydrochloride | Sigma (L5647-100G) | 1%, 2%, 3%, 4%, 5%, 10%, 15% in water; 5% and 10% in propylene glycol, 5% and 10% in water:propylene glycol (50:50; 90:10; 80:10 w/w) |
| Benzocaine | Sigma (E1501-100G) | 1%, 2%, 5% in acetone:propylene glycol (5:95 w/w); 1%, 2%, 5% in ethanol:propylene glycol (5:95 w/w) |
| Phenol in water | Sigma (P9346-100ML) | Added to 15% lidocaine solution to make 1% phenol. |
| Camphor | Sigma (148075-5G) | Can be added to above |

TABLE 2-continued

| Chemical tested/use | Supplier & Number | Concentrations |
|---|---|---|
| | | solutions to make from .05-.1% camphor. |
| Propylene glycol (1,2-propanediol) | Sigma (P4347-500ML) (meets USP testing specs) | Used to dissolve benzocaine and lidocaine. |
| Ethanol | Sigma (439844-500ML) | Used to dissolve benzocaine and lidocaine. |
| Acetone | Sigma (179124-500ML) | Used to dissolve benzocaine. |
| 5% Acetic Acid | commonly available | 2% acetic acid solutions (vinegar) were used to make 5% and 10% lidocaine solutions. |
| Ammonia | commonly available | gaseous ammonia dissolved in water (percentage not listed on bottle, probably 10%). |
| Meat tenderizer | commonly available | Granules dissolved in water to make a moist paste solution. |

Example 2

Procedures

Various formulations, as described below, were made with the above listed compounds, and made according to the following procedures.

Benzocaine was dissolved in either 2.5 ml of acetone or 2.5 ml of ethanol and then taken to 20 ml in propylene glycol. Lidocaine was dissolved in 2.5 ml of ethanol and then taken to 20 ml in propylene glycol. Lidocaine hydrochloride was generally dissolved in water. In one of the below examples lidocaine hydrochloride and benzocaine were dissolved in 2.5 ml of acetone and made up to 20 ml of propylene glycol to produce a 5% lidocaine hydrochloride and 5% benzocaine solution. For comparison a 10% lidocaine hydrochloride solution was made containing 2.5 ml of acetone and 17.5 ml of propylene glycol.

The following commercial sun-burn and sting-relief medications were purchased fresh in spray form, and applied according to manufacturer's recommendations: Lanacane® (active ingredients: benzethonium chloride 0.2%, benzocaine 20%), Bactine® (active ingredients: benzalkonium chloride 0.13% w/w, lidocaine 2.5% w/w), and CVS® Instant Burn Relief Spray (active ingredients: lidocaine 0.50%).

For examples 3-19, with the exception of the commercially available spray products and the meat tenderizer paste solution, all of the other test solutions were in liquid form and were applied using a one milliliter pipetter and sterile tips.

The above-described liquid formulations are examples of aqueous solutions of the present disclosure. Such formulations are suitable for topical application as a drop or spray to the affected area (e.g., skin at sting location).

The above formulations were prepared as described above, and the solution placed in an application bottle for drop application or for spray application. A formulation as prepared above would be applied, for treatment of an jellyfish sting on the arm, for example, in drop form in an amount of about 5-15 drops or about 0.5-1.5 ml, or sufficient amount to cover the affected area, applied to the affected area as soon as possible after the sting. Resolution of the condition would be signified by reduction and/or elimination of pain, redness, swelling and other irritation from the affected area.

For examples 3-19 below, the following general procedures were followed. Healthy, actively swimming jellyfish were used in all examples, and the same procedure was applied in all cases. The same human test subjects were used in all experiments, in order to have continuity and be able to qualitatively compare treatment effects among experimental dates.

Stings from sea wasps were induced by manually holding a live specimen by its bell, and dragging the tentacles across the inner forearm of the test subject. Sea-wasps caused immediate stinging sensations. Stings from the larger sea nettles were induced using tweezers to manually remove tentacles from living specimens and dragging them across the inner lower forearms of test subjects. Sea-nettle stings were of the same or somewhat more intensity as those of sea wasps, but were not felt until about 15 s after contact, perhaps because the tentacles have visibly thicker gelatinous coatings.

Products were applied to sting sites within 1-2 minutes unless otherwise noted below. Initial tests showed that multiple treatments on closely adjacent body regions could not be consistently discriminated. Thus one forearm was used for each treatment effect, and each forearm included two sting sites: one received a treatment while the other served as an untreated control. Tests were either conducted simultaneously in duplicate using two subjects, or sequentially several hours apart using the same subject.

Treatment effects were qualitatively defined into one of three categories: (a) treatment caused reduction in stinging sensation, substantially immediate relief, or both, relative to untreated control sites; (b) treatment caused an increase in stinging sensation, delayed relief, or both, relative to control sites; and (c) treatment was without effect.

Example 3

Comparison of Benzocaine, Lidocaine, and Anecdotal Remedies

In the present example a total of six treatments were tested:
deionized water
5% lidocaine in 80:20 water:propylene glycol
5% benzocaine in 90:10 propylene glycol:acetone
meat tenderizer (paste)
ammonia (store-bought full strength)
vinegar (acetic acid)(store-bought full strength)
Stinging jellyfish: sea wasps with 2" bell diameter
Results:
Deionized water and meat tenderizer were without effect. Ammonia and vinegar increased the initial pain, which then decreased similar to no treatment; this effect was perhaps due to irritation of the sting wounds or else triggering the firing of additional nematocysts still on the skin. Both lidocaine and benzocaine provided relief after about 1-2 minutes, and this relief was maintained until the stinging sensation eventually decreased in control sites (2-3 h). All treatments except for lidocaine and benzocaine resulted in an irritating and easily visible red rash within minutes of stinging; this rash was substantially reduced in the lidocaine and benzocaine treatments. No clear differences were observed between the lidocaine and benzocaine treatments. This test was repeated 4 h later with identical results.

Example 4

Comparison of Higher Concentrations of Lidocaine and Benzocaine

Two formulations according to the present disclosure were tested in the present example:
10% lidocaine in 50:50 water:propylene glycol
10% benzocaine in 90:10 propylene glycol:acetone
Stinging jellyfish: one large sea wasp with 3" bell diameter
Results:
Both formulations brought gradual pain relief within one minute, which seemed faster than the previous test at 5% concentrations of both products. Lidocaine brought sting relief more quickly than benzocaine, in 30-60 sec vs. 60-90 sec., and appeared to reduce redness at the sting site more than the benzocaine formulation. In contrast, pain/irritation at the control sites did not begin to decline until approximately 30 minutes after the sting, and required about 3 h to dissipate completely. The test was repeated 4 h later with identical results.

Example 5

Response Time of Lidocaine and Benzocaine

Two formulations were tested in the present example to test the minimum response time of the human body to topically applied lidocaine and benzocaine:
5 mg of pure benzocaine applied to the tongue
5 mg of pure lidocaine applied to the tongue
Results:
Both compounds caused localized numbness after 30 sec, and the numbness lasted about 15-30 min. The tongue is an extremely sensitive taste organ loaded with nerve cells, and the highest concentration possible of the pain relievers was tested. The observed response is interpreted to represent the minimum response time of the human body to topically applied lidocaine and benzocaine.

Example 6

Comparison of 5% vs. 10% Lidocaine in 80:20 Water:Propylene Glycol

Two formulations according to the present disclosure were tested:
5% lidocaine in 80:20 water:propylene glycol
10% lidocaine in 80:20 water:propylene glycol
Stinging jellyfish: one large sea wasp with 3" bell diameter
Results:
Both concentrations of lidocaine provided substantial pain relief and much quicker compared to no treatment. The rash was also somewhat less pronounced on the 10% compared to 5% solution, and the pain/irritation subsided faster.

Example 7

Effect of Acetic Acid in Combination With Lidocaine on Sting Relief

Two formulations were tested to compare treatment with and without acetic acid (vinegar), the anecdotally recommended treatment of choice:
10% lidocaine in 80:20 water:propylene glycol
10% lidocaine in 80:20 water:propylene glycol+10% acetic acid
Stinging jellyfish: sea wasps with 2" bell diameter
Results:
Lidocaine without acetic acid gave substantial relief in about 1 minute, compared to no treatment, in which stinging lasted for about 30 minutes. The acetic acid treatment actually stimulated initial pain before subsequently providing relief as in the treatment without acetic acid. Redness/physical irritation was greater in the acetic acid treatment indicating that acetic acid either antagonizes open sting wounds, fires more nematocysts, or both. The acetic acid is allegedly supposed to cause the un-fired nematocysts to fire, and thus prevent continued nematocyst firing after treatment is initiated (albeit with more initial pain). However it seems that the irritation of the acetic acid counteracts any benefit associated with immediate triggering of all of the nematocysts, at least in sea wasps.

Absence of lidocaine caused prolonged irritation (several hours) and redness, the latter being still visible the next day (20 h later). By comparison, lidocaine-treated sites were not red or irritated the next day. Its inclusion with 10% lidocaine is less effective than lidocaine alone.

The alcohol is a preservative and thus should prevent unfired nematocysts from firing. But the alcohol may instead enhance the pain because of its irritation of any the open wounds at the sting site.

Example 8

Effects of Deliberate Delay Before Application of Treatment

Two formulations according to the present disclosure were tested:
10% lidocaine in 80:20 water:propylene glycol applied immediately
10% lidocaine in 80:20 water:propylene glycol applied 5min after sting
Stinging jellyfish: sea wasp with 2" bell diameter
Results:
Lidocaine applied immediately provided relief as previously described in approximately 1 minute. A 5 minute delay before applying the lidocaine solution was judged uncomfortable, but the lidocaine then provided relief as though applied immediately.

This example was designed to mimic the delay that might be expected by a patient between the time of being stung and the time of sting product relief application. 10% lidocaine is effective in providing sting relief upon application, whether sooner or later although, the sooner it is applied, the sooner relief is felt.

Example 9

Comparison of Lidocaine in Water vs. Lidocaine in Propylene Glycol

Two formulations according to the present disclosure were tested:

10% lidocaine in water
10% lidocaine in 80:20 water:propylene glycol
Stinging jellyfish: sea nettle with 6" bell diameter
Results:

There was little difference between the two formulations. Although the performance of lidocaine in water only was slightly superior as judged by the test subjects, both formulations relieved pain as quickly as in previous tests, and much faster than the gradual disappearance of pain in the controls w/ no treatment.

Example 10

Effects of Alcohol in Sting-Relief Products

Two formulations according to the present disclosure were tested:
10% lidocaine in water+10% ethanol
10% lidocaine in 80:20 water:propylene glycol+10% ethanol
Stinging jellyfish: sea nettle with 5" bell diameter
Results:

Both formulations relieved stings much faster than untreated controls. However, sting relief by the formulation including alcohol was noticeably (several minutes) delayed, although eventually it alleviated pain much sooner than untreated sites.

Like acetic acid, alcohol did not improve treatment efficacy and seemed to increase the initial pain somewhat. This effect is likely due to the alcohol causing nematocyts to trigger, and/or aggravating any tiny open wounds caused by the nematocysts. However, the formulations including either alcohol or acetic acid (see above) did ultimately reduce pain to the same level as formulations without alcohol or acetic acid, but with a few minutes delay.

Example 11

Microscopy Observations of Nematocyst Responses to Product Exposure

Tentacles were removed using tweezers from an actively swimming sea nettle, placed in a glass Petri dish in seawater collected from the jellyfish tank (same salinity), and viewed at 60× under a zoom stereomicroscope while various liquid chemicals were pipetted directly onto the tentacles.
Results:

Vinegar stimulated mass firing of nematocysts. A 10% solution of lidocaine dissolved in seawater from the jellyfish container (same salinity) did not cause nematocysts from a new tentacle to fire. However, these same nematocysts, that did not fire when exposed to lidocaine, were shown not to be anaesthesized by the lidocaine formulation, because they fired immediately upon addition of vinegar. Plain seawater did not trigger nematocysts. These results suggest that vinegar, the anecdotal treatment of choice, triggers nematocyst firing in sea nettles. These results demonstrate that this is a chemical effect not a hydrodynamic one. Lidocaine does not trigger such a response, but it does not prevent the subsequent firing induced by a subsequent application of vinegar.

Example 12

Effects of Urea on Performance

Two formulations were tested to determine the effects of urea on the efficacy of formulations of the present disclosure.

10% lidocaine in water
10% lidocaine in water+10% urea
Stinging jellyfish: sea nettle with 4" bell diameter
Results:

There was no difference between the two formulations above, both provided relief within about 1 minute, and pain and redness diminished over time much faster than in untreated stings. The purpose of this example was to test the anecdotal notion that human urine can provide relief from jellyfish stings. However, urea did not appear to help or impede the soothing effect of lidocaine.

Example 13

Comparison of Lidocaine Only vs. Identical Concentration of Lidocaine:Benzocaine Mix Two formulations according to the present disclosure were tested:
10% lidocaine in acetone:propylene glycol
5% lidocaine+5% benzocaine, both dissolved in acetone:propylene glycol
Stinging jellyfish: sea nettle with 4" bell diameter
Results:

Interestingly, both treatments took longer to be effective compared to lidocaine dissolved in water only, presumably due to irritation of the wounds by acetone or the strong concentration of propylene glycol, and/or possible triggering of further nematocysts by the acetone. There was no clear distinction between the two above formulations.

Since benzocaine does not dissolve in water whereas lidocaine hydrochloride does, in the present example a compound that both compounds would dissolve in (acetone) was used in order to compare the pain relievers. While the two formulations did not appear to differ in providing pain relief, 10% lidocaine (as lidocaine hydrochloride) in water appears to be preferable because it appears that the alcohol, acetone, and/or vinegar used to dissolve the benzocaine in solution, are all at least somewhat associated with initial exacerbation of pain, likely due to increased nematocyst firings and/or wound irritation.

Example 14

Comparison of Three Commercially Available Pain Relief Sprays

Three commercially available pain relief sprays were tested in the present example for comparison to formulations of the present disclosure (ingredients listed above).
Bactine®
Lanacane®
CVS® Burn Relief Spray
Stinging jellyfish: sea nettle with 4" bell diameter
Results:

All three products either increased initial stinging sensation considerably, were ineffective, or both. The redness and irritation were also greater in the purchased products than with the formulations of the present disclosure tested above. Repeated spraying of Lanacane resulted in additional stinging w/ no subsequent relief. Despite containing various concentrations of lidocaine or benzocaine, these products were ineffective against nettle stings, and even appeared to induce additional nematocyst firing as a possible cause of the increased stinging sensation upon application, possibly due to the other ingredients contained in these products.

Example 15

Comparison of Lidocaine With and Without Propylene Glycol

Two formulations according to the present disclosure were tested:
10% lidocaine in water
10% lidocaine in 50:50 water:propylene glycol
Stinging jellyfish: sea nettle with 4" bell diameter
Results:
One purpose of this example was to determine if there was any pain relief benefit associated with propylene glycol. Both products continued to perform as previously described in the above example compared to untreated controls. The propylene glycol treatment has a higher initial stinging sensation, and thus a preference was observed for the water-only treatment. However, it may still be desirable to include propylene glycol for its anti-bacterial function.

Example 16

Comparison of 10% vs. 15% Lidocaine

Treatment:
10% lidocaine in water
15% lidocaine in water
Stinging jellyfish: sea nettle with 4" bell diameter
Results:
The formulation with 15% lidocaine acted faster (by about 10-15 sec) than 10% lidocaine, although the difference was not dramatic. Both products provided extended relief from irritation and redness.

Example 17

Comparison of Lidocaine With and Without Phenol

Two formulations according to the present disclosure were tested:
15% lidocaine in water
15% lidocaine in water+1% phenol
Stinging jellyfish: sea nettle with 4" bell diameter
Results:
No difference in sting alleviation was observed, both worked within about 1 minute, and both were far superior to no treatment. The odor of phenol is noticeable, and if used in the final product may be optionally covered by inclusion of camphor (about 0.05-0.1%) as fragrance.

Example 18

Effect of Low Concentration of Propylene Glycol on Lidocaine Sting Relief

Two formulations according to the present disclosure were tested:
15% lidocaine in water
15% lidocaine in water+15% propylene glycol
Stinging jellyfish: sea nettle with 4" bell diameter
Results:
This follows on the previous test with 50:50 water:propylene glycol. The propylene glycol treatment site had more initial irritation than the water-only lidocaine treatment, although both were superior to no treatment. Thus, it appears that propylene glycol may have a slight propensity to exacerbate the wounds like alcohol, ammonia, and vinegar.

Example 19

Effect of Various Concentrations of Lidocaine and/or Benzocaine on Time to Pain Relief The results on time to substantial pain relief for various formulations as described above, with varying concentrations of lidocaine or a lidocaine/benzocaine mixture were graphed. The data are presented in FIG. 1.

Example 20

Effect of 4% Lidocaine on Time to Pain Relief

In this example a composition of 4% lidocaine hydrochloride in water was tested according to the procedures set forth in Example 2 above. It was found that initial pain relief could be felt at around one minute after application, with complete or nearly complete relief at round 4.5 to 5 minutes from application of the composition.

Example 21

Beach Surveys Testing 4% Lidocaine Formulations on Extent of Relief

Figure 2:
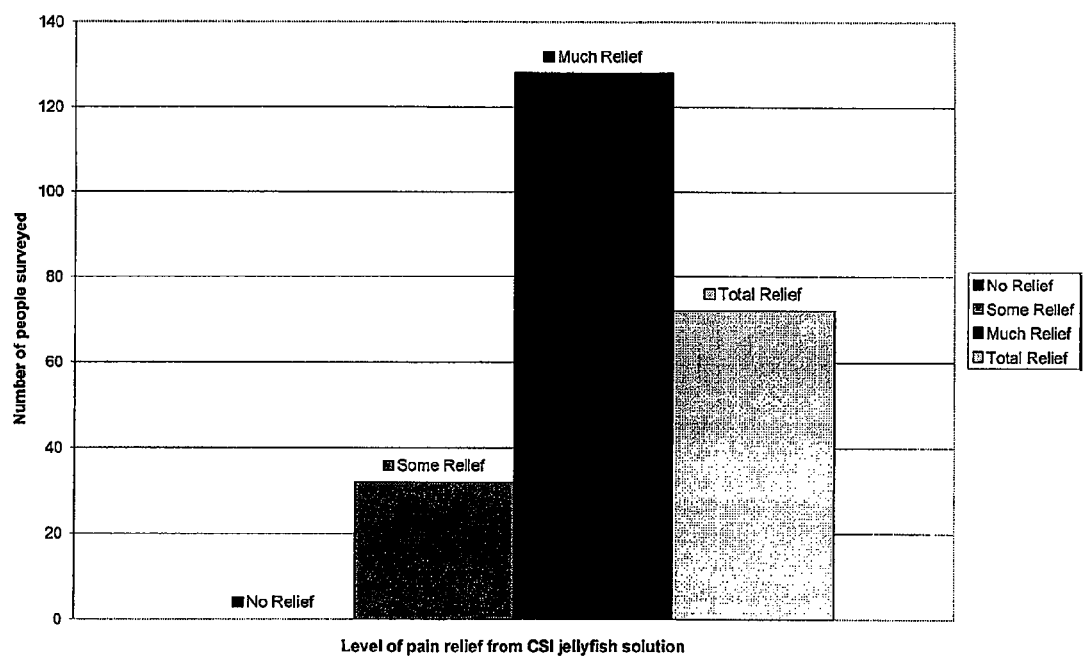
FIG. 2 illustrates a bar graph showing the number of subjects experiencing various levels of relief from the symptoms of jelly fish stings testing an embodiment of the present disclosure including 4% lidocane and water.

The beach surveys were conducted on beachgoers that stated they had been stung by a jellyfish. All participants voluntarily filled out an 8 question survey.
Formulations: All beach surveys were conducted at 4% Lidocaine and water with a pump or trigger spray application.
Locations: Tybee Island, Ga., Saint Simons Island, Ga., Hilton Head, S.C., Jacksonville beach, Fla., Daytona beach, Fla.
Time to application: Varied based on the person surveyed. Average times from sting to treatment ranged from 5 to 15 minutes.
Application to relief: Most respondents noted that they began to feel relief at the 1 minute mark. Based on an average level of affected area (less than 10% body coverage) the respondents noted virtually all the pain subsided by the 5 minute mark. (Most of the respondents who noted "some relief" departed within 2 minutes, which is the approximately time it took them to fill out the survey. Some of these respondents later returned to report total relief, but this is not shown in the data below). The results are presented in Table 3 and FIG. 2, below (total respondents: 232).

TABLE 3

| Relief documented by Surveys | |
|---|---|
| No relief | 0 |
| Some relief | 32 |
| Much relief | 128 |
| Total relief | 72 |

Example 22

Effect of 4% Lidocaine Formulation on Chigger Bites

The subject for this example had substantial experience with chigger bites, with typical symptoms including intense and prolonged (days to weeks) itching associated with the bites. Subject was provided with a solution of 4% lidocaine and water (carrier) according to the present disclosure. Subject received 6 chigger bites on inner thigh area. Subject applied the formulation to two of the chigger bites, treated two others with Chigger Rid®, a drug store product, and applied clear finger nail polish, a home remedy, to the final two bites. Subject reported that the two treated with the formulation of the present disclosure ceased itching within minutes of application with no further symptoms. Subject reported that the remaining 4 bites continued to itch. After three days, subject removed the other two products and applied the 4% lidocaine formulation of the present disclosure to the remaining four bites. Subject reported that the itching in the affected area of the remaining 4 bites subsided after application of the formulation of the present disclosure and did not return.

Example 23

Effect of 4% Lidocaine Formulation on Fire Ant Bites

The subject for this example had substantial experience with fire ant bites, with general symptoms of blistering, itching, pain associated with the bites. Subject was provided with a solution of 4% lidocaine and water (carrier). Subject received 7 fire ant bites while gardening outside. Subject applied the formulation to the seven bites approximately 15 minutes after the bites occurred. Subject reported complete relief from pain and itching after application and that the typical blisters did not form.

I claim:
1. A method of treating a jellyfish sting comprising administering to a host in need of treatment a composition consisting of:
   at least about 2.75 weight percent of lidocaine or a pharmaceutically acceptable salt thereof;
   from 0 to about 1 weight percent of an optional antiseptic compound;
   from 0 to about 0.1 weight percent of an optional fragrance;
   from 0 to about 0.05 weight percent of an optional aloe extract; and
   water as a pharmaceutically acceptable carrier.
2. The method of claim 1, wherein the antiseptic compound is selected from benzalkonium chloride, DMDM hydantoin, methyl paraben, propyl paraben, and combinations thereof.
3. The method of claim 1, wherein the fragrant compound is selected from camphor and eucalyptus oil.
4. The method of claim 1, wherein:
   the antiseptic compound is selected from benzalkonium chloride, DMDM hydantoin, methyl paraben, propyl paraben, and combinations thereof; and
   the fragrant compound is selected from camphor and eucalyptus oil.

* * * * *